US006221901B1

(12) United States Patent
Shrivastava et al.

(10) Patent No.: US 6,221,901 B1
(45) Date of Patent: Apr. 24, 2001

(54) MAGNESIUM (-)HYDROXYCITRATE, METHOD OF PREPARATION, APPLICATIONS, AND COMPOSITIONS IN PARTICULAR PHARMACEUTICAL CONTAINING SAME

(76) Inventors: Ravi Shrivastava, 43bis route de Chateaugay, 63118 Cebazat (FR); Patrick Lambropoulos, 35 Traverse Nicolas, 13007 Marseille (FR)

( * ) Notice: Subject to any disclaimer, the term of this patent is extended or adjusted under 35 U.S.C. 154(b) by 0 days.

(21) Appl. No.: 09/284,864

(22) PCT Filed: Oct. 17, 1997

(86) PCT No.: PCT/FR97/01860

§ 371 Date: Apr. 22, 1999

§ 102(e) Date: Apr. 22, 1999

(87) PCT Pub. No.: WO98/17671

PCT Pub. Date: Apr. 30, 1998

(30) Foreign Application Priority Data

Oct. 22, 1996 (FR) .................................................. 96 13094

(51) Int. Cl.[7] .......................... A61K 31/19; A61K 31/34; A61K 31/355

(52) U.S. Cl. .......................... 514/458; 514/184; 514/185; 514/186; 514/458; 514/474; 514/574; 562/580; 562/582

(58) Field of Search ...................................... 514/574, 184, 514/185, 186, 458, 474; 562/580, 582

(56) References Cited

U.S. PATENT DOCUMENTS

| 3,671,583 | * | 6/1972 | Griot et al. ........................ 260/535 P |
| 5,536,516 | * | 7/1996 | Moffett et al. ....................... 426/271 |
| 5,626,849 | * | 5/1997 | Hastings et al. .................. 424/195.1 |

FOREIGN PATENT DOCUMENTS

| 2 716 374 | * | 8/1995 | (FR) . |
| 2 733 418 |   | 10/1996 | (FR) . |

OTHER PUBLICATIONS

Barth et al., Chem. Abstr. 77:70871, 1972.*
Gabriel et al., Chem. Abstr. 114:117620, 1991.*
Chemical Abstracts, vol. 124, No. 8, 1996, Columbus, Ohio, US; abstract No. 97375r, p. 743, col. 1, XP002034986. R.P. Singh et al., Biol. Mem., vol. 21, No. 1, 1995, pp. 27–33.

* cited by examiner

*Primary Examiner*—Peter O'Sullivan
(74) *Attorney, Agent, or Firm*—Browdy and Neimark

(57) ABSTRACT

Magnesium (–)hydroxycitrate, preparation process, dietary and therapeutic uses particularly in the cardiovascular field, and compositions in particular pharmaceutical containing it.

23 Claims, No Drawings

MAGNESIUM (-)HYDROXYCITRATE, METHOD OF PREPARATION, APPLICATIONS, AND COMPOSITIONS IN PARTICULAR PHARMACEUTICAL CONTAINING SAME

CROSS REFERENCE TO RELATED APPLICATION

The present application is the national stage under 35 U.S.C. 371 of PCT/FR97/01860, filed Oct. 17, 1997.

FIELD OF THE INVENTION

The present invention relates to a new (-)hydroxycitrate compound, its preparation process and the compositions containing it.

BACKGROUND OF THE INVENTION (-)hydroxycitrate ((-)hydroxycitric acid or also Garcinia acid) is the active ingredient obtained from the extract of Garcinia indica or Garcinia cambogia, trees found in southeast Asia and in particular in southern India.

These two species of plant directly contain a (-)stereoisomer of hydroxycitrate. The extract of the fruit of these two plants is widely used in traditional Indian medicine for treating various diseases.

A mixture of (-)hydroxycitrate and chromium is commercialized in the United States as a dietary product for combatting excess weight and obesity, under the name of Citrin®.

Known pharmacological activities and processes for preparing (-)hydroxycitrate from fruit are already described in the literature.

This product is further commercialized by different manufacturers such as the FLUKA company.

Majeed M. et al. in "CITRIN®: a revolutionary herbal approach to weight management", New Editions Publishing, 1675 Rollins Road, Burlingame, Calif. 94010, Pages 1–69, 1994, describes a certain number of studies which show that (-)hydroxycitrate reduces body weight by reducing the synthesis of fatty material.

Many people throughout the world, for example approximately 4 million people in France, suffer from hypercholesterolemia. When the levels of circulating cholesterol exceed normal levels, due to the peroxidation of lipids, the cholesterol and cholesterol esters are capable of accumulating in the cells of arterial smooth muscles, provoking their proliferation, the accumulation of lipids on the artery wall (atheroma), which may lead to the formation of thrombus, followed by the blocking of coronary or cerebral arteries.

Existing treatments (fibrates, HMG coenzyme-A reductase inhibitors, etc.) aim to reduce levels of circulating cholesterol but play no protective role in the pathological effects of cholesterol on the artery wall, either by reducing proliferation or by inhibiting the accumulation of cholesterol in the cells of arterial smooth muscles.

Furthermore, owing to their side effects, such as hepatic or renal insufficiency, these medicaments are used only when the levels of circulating cholesterol greatly exceed physiological limits.

It would therefore be desirable to find a product endowed with the following properties:

capable of reducing the synthesis of cholesterol, capable of inhibiting the accumulation of lipids in the cells of vascular smooth muscles, capable of aiding the elimination of lipids which have accumulated in the cells of vascular smooth muscles, capable of reducing cell proliferation due to the reduction in intracellular lipids, endowed with a sufficient therapeutic margin, and devoid of side effects or toxic effects at high doses.

SUMMARY OF THE INVENTION

For this reason, a subject of the present invention is a new compound of (-)hydroxycitrate, namely magnesium (-)hydroxycitrate, in particular crystallized magnesium (-)hydroxycitrate, quite particularly substantially pure.

A subject of the present invention is also a process for the preparation of magnesium (-)hydroxycitrate, characterized in that an extract of Garcinia cambogia is reacted with an aliphatic alcohol in order to obtain a precipitate which is subjected to the action of a tannin fixing agent, the solids are eliminated and the supernatant is recovered and subjected to batch chromatography on an anion exchanger resin, then left in contact under agitation, the supernatant is eliminated followed by elution of the magnesium (-)hydroxycitrate, the eluate is dried in order to obtain the expected magnesium (-)hydroxycitrate.

Under preferential conditions for the implementation of the process described above, the aliphatic alcohol is a $C_1$–$C_6$ alcohol, preferably propanol, isopropanol or ethanol, the tannin fixing agent is a Polypyrrolidone derivative, preferably Polyvinyl Polypyrrolidone, elimination of the solids is carried out by centrifugation, the anion exchanger resin is preferably a DEAE SEPHADEX A50 resin, drying of the eluate is carried out by lyophilization.

Magnesium (-)hydroxycitrate has very useful pharmacological properties. It is in particular endowed with remarkable hypolipemia, anticholesterol, antiatheromatous and antioxidant properties in particular with espect to free radicals. It is in particular capable of reducing cholesterol synthesis, inhibiting the accumulation of lipids in the cells of vascular smooth muscles, aiding the elimination of lipids accumulated in the cells of the vascular smooth muscles, reducing cell proliferation due to the reduction in intracellular lipids, and as a result, reducing the deposit of fats on the vascular endothelium. It is further endowed with antistress, antifatigue and cell regeneration properties. It has also been found to be endowed with antihypertensive properties.

These properties are illustrated below in the experimental part. They justify the use of magnesium (-)hydroxycitrate as a medicament.

The medicaments according to the present invention are used for example in both the curative and preventative treatment of pathologies caused by the local accumulation of lipids or by an increase in the circulating cholesterol level, which causes diseases such as vascular stenosis, lipidic striae, the formation of atheroma, thrombosis and vascular diseases affecting both macro- and microcirculation as well as hypercholesterolemia.

They are also used in ageing disorders linked to the effects of oxidants such as free radicals.

They are also used in both the curative and the preventative treatment of arterial hypertension.

The usual dose, which may vary according to the patient treated and the affliction in question, can be, for example from 100 to 1000 mg of magnesium (-)hydroxycitrate per day by oral route in human, for at least 20 days.

A subject of the invention is also pharmaceutical compositions containing at least magnesium (−)hydroxycitrate as active ingredient.

In these compositions, the active ingredient is advantageously present at effective physiological doses; the aforementioned compositions contain in particular an effective antihypercholesterolemia or antihypertensive dose of at least one active ingredient above.

As medicaments, magnesium (−)hydroxycitrate can be incorporated in pharmaceutical compositions intended for administration by the digestive or parenteral route.

These pharmaceutical compositions can be, for example, solid or liquid and be presented in the pharmaceutical forms commonly used in human medicine, such as for example plain or sugar-coated tablets, capsules, granules, caramels, suppositories, injectable preparations, creams, lotions or gels; they are prepared according to the usual methods. They may incorporate the active ingredient(s) with excipients usually used in these pharmaceutical compositions such as talc, gum arabic, lactose, starch, magnesium stearate, cocoa butter, aqueous or non-aqueous vehicles, fatty matter of animal or vegetable origin, paraffin derivatives, glycols, various wetting, dispersing or emulsifying agents, preservatives.

The Applicant has further discovered that magnesium (−)hydroxycitrate was capable of potentiating the effects of minerals, in particular of metals involved in physiological enzymatic reactions, quite particularly zinc, copper, manganese, selenium and silicon, and was also capable of potentializing the effects of vitamins, particularly vitamins A, C and E.

But while the aforementioned mineral and vitamin products showed slight protective effects with respect to hypercholesterolemia, these effects are not at a sufficient level to envisage therapeutic use. However, potentiated by magnesium (−)hydroxycitrate, they have quite surprising effects.

For this reason, a further subject of the present invention is a synergistic combination, characterized in that it comprises magnesium (−)hydroxycitrate and at least one metal, in ionized or non-ionized form, preferably in the form of a cation, chosen from the group consisting of the following metals: magnesium, copper, cobalt, zinc, nickel, selenium, silicon, manganese, lithium and iron, or magnesium (−)hydroxycitrate and at least one vitamin, in particular an antioxidant vitamin.

Preferred synergistic combinations according to the invention include magnesium (−)hydroxycitrate and at least two metals, in particular two cations chosen from the aforementioned group and/or at least two vitamins.

Under preferential conditions, the constituents of the synergistic combination according to the invention are present in the following proportions by weight: for one part of magnesium (−)hydroxycitrate, 0.1 to 2 parts of a mineral salt or a metal oxide above and/or 0.1 to 1 part of vitamin(s), it being specified that, in a mineral salt or an oxide, the metal can represent from 2 to 50% by weight, preferably 5 to 40%, particularly 10 to 35%, with respect to the weight of the compound in question.

Among the aforementioned metals selenium and silicon are preferred, preferably in the form of cations.

The anions with which the above cations can be combined are pharmaceutically acceptable anions such as for example those derived from the following acids: hydrochloric, hydrobromic, nitric, sulphuric, phosphoric, acetic, formic, propionic, benzoic, maleic, fumaric, succinic, tartaric, citric, oxalic, glyoxylic, aspartic, alkane sulphonics such as methane or ethane sulphonic acids, arylsulphonics, such as benzene or paratoluene sulphonic or carboxylic acids, or gluconic acid.

As vitamins, vitamins A, C and E are preferably retained and in particular vitamins A and E.

The combinations according to the present invention are preferably presented in unit doses each comprising at least 50 mg of magnesium (−)hydroxycitrate, preferably at least 100 mg of magnesium (−)hydroxycitrate, and quite particularly approximately 250 mg of magnesium (−)hydroxycitrate. Advantageously, a unit dose comprises at the most 1 g of magnesium (−)hydroxycitrate. In particular, a unit form is presented under a volume of less than 20 cm$^3$, in particular less than 10 cm$^3$, and quite particularly less than 1 cm$^3$.

The combinations which are a subject of the present invention have the same very useful pharmacological properties as those of magnesium (−)hydroxycitrate.

These properties are illustrated below in the experimental part. They therefore justify the use of the combinations described above as a medicament.

The usual dose, which varies according to the patient treated and the affection in question, can be, for example, from 100 to 1000 mg of magnesium (−)hydroxycitrate per day by oral route in man, for at least 20 days, combined with 2 to 40 mg of colloidal silica and 100 to 1500 mg of selenium or magnesium gluconate.

A subject of the present invention is also a process for the preparation of a combination as defined above, characterized in that magnesium (−)hydroxycitrate is mixed with at least one metal in ionized or non-ionized form or with at least one aforementioned antioxidant vitamin.

A subject of the present invention is also a combination containing magnesium (−)hydroxycitrate or a combination of magnesium (−)hydroxycitrate and at least one metal in ionized or non-ionized form chosen from the group consisting of the following metals: magnesium, copper, cobalt, zinc, nickel, selenium, silicon, manganese, lithium and iron, or of (−)hydroxycitrate and at least one vitamin, in particular an antioxidant vitamin, as a medicament, i.e. magnesium (−)hydroxycitrate or a combination of the above compounds for its use in a therapeutic, curative or preventative treatment method for the human or animal body.

As a therapeutic treatment, there can in particular be mentioned the known uses and indications of these metals or vitamins; in fact, their effects are potentiated by magnesium (−)hydroxycitrate.

A further subject of the present invention is the use of magnesium (−)hydroxycitrate or a combination containing magnesium (−)hydroxycitrate and at least one metal in ionized or non-ionized form chosen from the group consisting of the following metals: magnesium, copper, cobalt, zinc, nickel, selenium, silicon, manganese, lithium and iron, or magnesium (−)hydroxycitrate and a vitamin, in particular an antioxidant vitamin, as a dietary product, nutritional supplement or nutritional adjuvant or also as a cosmetic product.

A subject of the invention is therefore also dietary, nutritional or cosmetic compositions containing magnesium (−)hydroxycitrate or a combination above.

A further subject of the present invention is magnesium (−)hydroxycitrate or a synergistic combination of magnesium (−)hydroxycitrate and at least one metal chosen from the group consisting of the following metals: magnesium, copper, cobalt, zinc, nickel, selenium, silicon, manganese, lithium and iron, or magnesium (−)hydroxycitrate and/or at least one vitamin, in particular an antioxidant vitamin, for the preparation of a medicament intended for the treatment of a cardiovascular disease, in particular intended for the treatment of a localized or generalized pathology caused by cholesterol or of hypertension.

Under preferential implementation conditions, the medicament intended for the treatment of a cardiovascular disease above is a medicament with lipid antioxidant properties.

Under quite particularly preferred conditions, the above medicament is intended for the treatment of hypercholesterolemia and the pathologies caused by it or for the treatment of arterial hypertension.

DETAILED DESCRIPTION OF THE INVENTION

The following examples illustrate the present Application.

EXPERIMENTAL PART

EXAMPLE 1

Preparation of Magnesium (–)Hydroxycitrate 1 kg of a 30% extract of *Garcinia cambogia* (supplier GREENTECH, St Beauzire—France) titrant 60 g/l hydroxycitric acid is reacted with 2 liters of ethanol in order to obtain a precipitate which is subjected to the action of 50 g of polyvinyl polypyrrolidone, the reaction medium is agitated for 30 minutes, the solids are eliminated by centrifugation at 6000 g for 15 minutes, and the supernatant is recovered. The latter is subjected to batch chromatography on 200 g of DEAE SEPHADEX A 50 anion exchanger resin equilibrated at pH 3, 0.1M NaCl (1 g of resin per 1.5 mole of acid), agitation is carried out for 16 hours followed by decanting, the supernatant is eliminated followed by eluting with 1000 ml of a 0.5 M solution of magnesium chloride, agitation is carried out for 4 hours, the eluate is recovered and dried, and 70 g of expected product is obtained.

EXAMPLE 2

Tablets were prepared corresponding to the following formula:

| | |
|---|---|
| magnesium (-)hydroxycitrate (active ingredient) | 300 mg |
| magnesium gluconate | 360 mg |
| colloidal silica | 7.5 mg |
| excipient s.q. for a tablet completed at | 1000 mg |
| (detail of excipient: lactose, starch, talc, magnesium stearate). | |

EXAMPLE 3

Divisible tablets were prepared corresponding to the following formula:

| | |
|---|---|
| magnesium (-)hydroxycitrate | 150 mg |
| selenium | 5 mg |
| vitamin E | 75 mg |
| excipient s.q. for a tablet completed at | 250 mg |
| (detail of excipient: lactose, starch, talc, magnesium stearate). | |

EXAMPLE 4

Divisible tablets were prepared corresponding to the following formula:

| | |
|---|---|
| magnesium (-)hydroxycitrate | 375 mg |
| colloidal silica | 7.5 mg |
| selenium | 40 mg |
| excipient s.q. for a divisible tablet completed at | 1000 mg |

EXAMPLE 5

Ampoules to be drunk were prepared corresponding to the following formula:

| | |
|---|---|
| magnesium (-)hydroxycitrate | 300 mg |
| magnesium gluconate | 100 mg |
| selenium | 40 mg |
| excipient s.q. for an ampoule completed at | 10 ml |
| (detail of excipient: distilled water) | |

EXAMPLE 6

Sachets for a suspension to be drunk were prepared corresponding to the following formula:

| | |
|---|---|
| magnesium (-)hydroxycitrate | 500 mg |
| magnesium gluconate | 100 mg |
| excipient s.q. for a sachet completed at | 5 g |
| (detail of excipient: lactose) | |

EXAMPLE 7

Sachets for a suspension to be drunk were prepared corresponding to the following formula:

| | |
|---|---|
| magnesium (-)hydroxycitrate | 250 mg |
| magnesium gluconate | 150 mg |
| excipient s.q. for a sachet completed at | 5 g |
| (detail of excipient: lactose) | |

Pharmacological Study

1) Study of the Mortality of Human Epithelial Cells and of Rat Arterial Smooth Muscle Cells.

The antioxidant effects of (–)hydroxycitrate and of different minerals were tested according to the protocol described by Michiels et al: "A new experimental model to study oxygen toxicity", Arch. int. Physiol. Biochem. 94 (5), S13–S18, 1986, using rat hepatocytes, as well as human epithelial cells and rat arterial smooth muscle cells.

The inhibitory effects of these compounds on the proliferation of arterial smooth muscle and on the accumulation of intracellular lipids was also tested using the method described by Shrivastava et al. in Meth. Find. Exp. Clin. Pharmacol. 15 (6), pages 345–350, 1993.

The various products were respectively tested at the following concentrations:

(–)hydroxycitrate 0.1 mM silicon 0.036 mM magnesium 0.1 mM in the culture medium.

The following results were obtained:

REDUCTION IN PERCENTAGES

| Product tested | Cell mortality | Accumulation of lipids | Proliferation of cells |
|---|---|---|---|
| (−)hydroxycitrate | 0 | 16 (±3) | 6 (±4) |
| Magnesium | 6 (±3) | 20 (±9) | 2 (±2) |
| Silicon | 28 (±7) | 32 (±5) | 28 (±6) |
| Magnesium (−)hydroxycitrate | 70 (±8) | 81 (±13) | 48 (±8) |

It can be observed firstly that the (−)hydroxycitrate alone has no protective effect on cell mortality. Magnesium alone reduces this mortality very slightly, whereas magnesium (−)hydroxycitrate has a more protective effect.

The magnesium (−)hydroxycitrate greatly reduces cell mortality (70±8%), proving the protective effect of this product against oxidation damage.

As regards the accumulation of lipids and cell proliferation, a very significant increase in the effects of magnesium (−)hydroxycitrate is observed with respect to (−)hydroxycitrate or magnesium.

These results are quite unexpected.

2) Study of the Effect in vivo on the Cholesterol Level and on Lipidic Deposits in Hypercholesterolemic Rabbits.

Two batches of 20 male rabbits (Elevage scientifique des Dombes: 2.5–3 kg) received a cholesterol-rich food (1%) for a period of 8 weeks. The first batch were not treated and therefore served as a control while the second batch received 750 mg/kg of magnesium (−)hydroxycitrate by oral route. The lipidic analyses after 4 weeks of treatment showed a reduction in LDL's and an increase in HDL's in rabbits which received magnesium (−)hydroxycitrate.

|  | HDL's in g/l | LDL's in g/l | Total cholesterol in g/l | Total cholesterol/ HDL ratio |
|---|---|---|---|---|
| Controls + | 0.224 | 5.17 | 5.55 | 26.78 |
| Magnesium (−)hydroxycitrate | 0.246 | 4.00 | 4.47 | 19.22 |
|  | +8.5% | −22.4% | −19.5% | −28.2% |

Analyses carried out on the wall of the aorta after 4 weeks (10 rabbits) and after 8 weeks (10 rabbits) showed a reduction in the number of lipidic deposits in the rabbits which received magnesium (−)hydroxycitrate.

|  | Controls + | Magnesium (−)hydroxycitrate | Variation % |
|---|---|---|---|
| Aortic arch |  |  |  |
| Week 4 | 9.5 | 3.5 |  |
| Week 8 | 14.0 | 1.5 |  |
| Thoracic arch |  |  |  |
| Week 4 | 0.0 | 0.0 |  |
| Week 8 | 2.0 | 0.0 |  |
| Total | 25.5 | 5.0 | −80.4% |

3) Study of Antiatherosclerotic Effects in the Hypercholesterolemic Rabbit.

Two batches of 15 male rabbits (Elevage scientifique des Dombes: 2.5–3 kg) received a cholesterol-rich food: 0.2% for the period D+8 to D+37, then 1% until D+69, when the animals are sacrificed.

The first batch was not treated and therefore served as a control while the second batch received 500 mg/kg of magnesium (−)hydroxycitrate by oral route. Analyses after the end of treatment showed that administration of magnesium (−)hydroxycitrate by oral route at a dose of 500 mg/kg/day in hypercholesterolemic rabbits for 62 days has the following effects:

No deaths

Well tolerated

No noticeable effect on food consumption or body weight compared with the controls No modification in hematological parameters Reduction in hepatic enzymes indicating a hepatoprotective effect in the batch treated Reduction in the total cholesterol level (−13.75%), in LDL's (16.36%) and in the total cholesterol/HDL ratio (−25.72%) with an increase in HDL levels (+12.5%) in the rabbits treated with respect to the controls.

Reduction in weight of heart, liver, spleen (−20.3%) and surrenal glands (−21.6%) in the batch treated, indicating a protective effect against hypercholesterolemia on these organs and a resulting reduction in stress Reduction of 46.3% in lipidic deposits on the aortic vascular wall in the batch treated with respect to the control batch.

These results show that magnesium hydroxycitrate has a hypocholesterolemia and anti-atherosclerotic effect at non-cytotoxic doses on the hypercholesterolemic rabbit.

4) Study of Anti-hypertensive Activity in the Hypertensive Rat

Magnesium (−)hydroxycitrate was tested on 12 hypertensive rats. A batch of 12 other hypertensive rats was used as a control batch. An average reduction in arterial pressure of 17%±3% with respect to the controls (untreated) was noted after one week of treatment at a rate of 500 mg per kilogram per day by oral route.

5) Toxicity

The toxicity of magnesium (−)hydroxycitrate is greater than 2 g/kg by intraperitoneal route or than 7 g/kg per os in the rat. That of metals, in particular in the form of salts or mineral oxides (frequently administered as trace elements) is well known.

What is claimed is:

1. A composition comprising magnesium (−)hydroxycitrate and at least one metal in ionized or non-ionized form, selected from the group consisting of magnesium, copper, cobalt, zinc, nickel, selenium, silicon, manganese, lithium and iron.

2. A composition according to claim 1, comprising at least two metals selected from the group consisting of magnesium, copper, cobalt, zinc, nickel, selenium, silicon, manganese, lithium and iron.

3. A composition according to claim 1, in the form of a unit dose comprising at least 50 mg of magnesium (−)hydroxycitrate.

4. A composition according to claim 1, comprising, by weight, for one part of magnesium (−)hydroxycitrate, 0.1 to 2 parts of a mineral salt or a metal oxide.

5. A composition according to claim 2 in unit dosage form further comprising at least 50 mg of said magnesium (−)hydroxycitrate.

6. A composition according to claim 5 comprising, by weight, for one part of said magnesium (−)hydroxycitrate, 0.1 to 2 parts of a said metal in oxide or mineral salt form; or, for one part of said magnesium (−)hydroxycitrate, 0.1 to 1 part of at least one said vitamin.

7. A composition according to claim 2 comprising, by weight, for one part of said magnesium (−)hydroxycitrate, 0.1 to 2 parts of a said metal in oxide or mineral salt form; or, for one part of said magnesium (−)hydroxycitrate, 0.1 to 1 part of at least one said vitamin.

8. A composition according to claim 3 comprising, by weight, for one part of said magnesium (−)hydroxycitrate, 0.1 to 2 parts of a said metal in oxide or mineral salt form; or, for one part of said magnesium (−)hydroxycitrate, 0.1 to 1 part of at least one said vitamin.

9. In a method for the preparation of a medicament for the treatment of a cardiovascular disease and comprising a cardiovascular-effective compound in a quantity sufficient to provide a cardiovascular effect, the improvement wherein magnesium (−)hydroxycitrate is used as said cardiovascular-effective compound or as at least one said cardiovascular-effective compound.

10. In a method of treating a cardiovascular disease in a patient in need thereof with a cardiovascular-effective compound, the improvement comprising using magnesium (−)hydroxycitrate in a cardiovascular-effective amount in said method.

11. In a method of administering a dietary or nutritional product to a subject, the improvement wherein said dietary or nutritional product comprises magnesium (−)hydroxycitrate or a combination according to claim 1.

12. In a method of administering a dietary or nutritional product to a subject, the improvement wherein said dietary or nutritional product comprises a combination according to claim 2.

13. In a method of applying a cosmetic product to a subject, the improvement wherein said cosmetic product includes magnesium (−)hydroxycitrate in a cosmetic-effective amount, or a combination according to claim 1.

14. In a method of applying a cosmetic product to a subject, the improvement wherein said cosmetic product includes a combination according to claim 2.

15. A process for preparing magnesium (−)hydroxycitrate comprising reacting an extract of *Garcinia cambogia* with an aliphatic alcohol to form a precipitate;

contacting said precipitate with a tannin fixing agent to form a mixture of solids and a supernatant;

eliminating the solids from said mixture and recovering the supernatant;

subjecting the supernatant to batch chromatography on an ion exchange resin;

maintaining said ion exchange treated supernatant in contact with said ion exchange resin;

removing the supernatant and eluting magnesium (−)hydroxycitrate therefrom;

and drying the eluate to obtain magnesium (−)hydroxycitrate.

16. A composition comprising magnesium (−)hydroxycitrate and at least one vitamin.

17. A composition according to claim 16 comprising by weight, of one part of magnesium (−)hydroxycitrate, 0.1 to 1 part by weight of at least one vitamin.

18. In a method for treating arterial hypertension in a patient in need thereof, the improvement comprising using magnesium (−)hydroxycitrate in an effective amount to treat arterial hypertension in said method.

19. In a method for treating athermatony disease in a patient in need thereof, the improvement comprising using magnesium (−)hydroxycitrate in an effective amount to treat accumulation of lipids in cells of vascular smooth muscles.

20. A method for treating hypercholesterolemia comprising administering to a patient in need thereof an effective amount of magnesium (−)hydroxycitrate.

21. The method according to claim 20 further administering to said patient an effective amount of at least one metal selected from the group consisting of magnesium, copper, cobalt, zinc, nickel, selenium, silicon, manganese, lithium, and iron.

22. The method according to claim 20 further administering to said patient an effective amount of magnesium and at least one vitamin.

23. The method according to claim 22 wherein the at least one vitamin is an antioxidant vitamin.

\* \* \* \* \*